US00PP15522P3

(12) United States Plant Patent
Yamaguchi

(10) Patent No.: US PP15,522 P3
(45) Date of Patent: Feb. 1, 2005

(54) *PACHYCENTRIA FORMOSANA* PLANT NAMED 'GIFU VARIEGATED'

(50) Latin Name: *Pachycentria formosana*
Varietal Denomination: Gifu Variegated

(75) Inventor: Seiju Yamaguchi, Mizunami (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/153,089

(22) Filed: May 22, 2002

(65) Prior Publication Data

US 2003/0221232 P1 Nov. 27, 2003

(51) Int. Cl.[7] ..... A01H 5/00

(52) U.S. Cl. ..... Plt./263

(58) Field of Search ..... Plt./263

*Primary Examiner*—Anne Marie Grunberg
*Assistant Examiner*—Annette H Para
(74) *Attorney, Agent, or Firm*—Christie, Parker & Hale, LLP

(57) ABSTRACT

A new plant variety of *Pachycentria formosana* characterized by its pink and white variegated new foliage, and white variegated mature foliage.

2 Drawing Sheets

Classification: the present invention relates to a new *Pachycentria formosana* plant.

Varietal denomination: The varietal denomination of the new variety is 'Gifu Variegated'.

BACKGROUND OF THE INVENTION

The present invention relates to a new and distinct variety of *Pachycentria Blume, Pachycentria formosana* Hayata, and was discovered as a branch sport of an unnamed variety of *Pachycentria formosana* Hayata (unpatented) in Mizunami-shi, Gifu Prefecture, Japan by the originator, Mr. Seiju Yamaguchi.

The genus *Pachycentria* is included in the family Melastomataceae that comprises about 240 genera and about 3000 species of mostly tropical herbs, shrubs, and trees in both hemispheres. *Pachycentria* comprises about 10 species of shrubs native to Southeast Asia. *Pachycentria formosana* Hayata is endemic in Taiwan. The genus is distinguished from other genera in the Melastomataceae by a small ovary in an urceolate hypanthiumn, and by seeds with comb-shaped testa cells.

SUMMARY OF THE INVENTION

The new variety was discovered as a branch sport, and differs from other cultivars known to the inventor by its pink and white variegated new foliage, and white variegated mature foliage. Asexual reproduction of the new variety by stem cuttings in Gifu Prefecture, Japan; Lewisberry, Pa.; and Vacaville, Calif.; have confirmed that the distinctive characteristics of the new variety are stable and transmitted to succeeding generations, and the new variety reproduces true to type.

COMPARISON WITH PARENT

'Gifu Variegated' is distinguished from its parent and all other varieties of *Pachycentria formosana* of which I am aware by its pink and white variegated new foliage, and white variegated mature foliage.

BRIEF DESCRIPTION OF ILLUSTRATION

The accompanying photographic illustration shows a plant of the new cultivar as true to color as is reasonably possible to make in an illustration of this character.

FIG. 2 illustrates the flower of the new variety.

DETAILED DESCRIPTION OF THE NEW VARIETY

Figure 1:
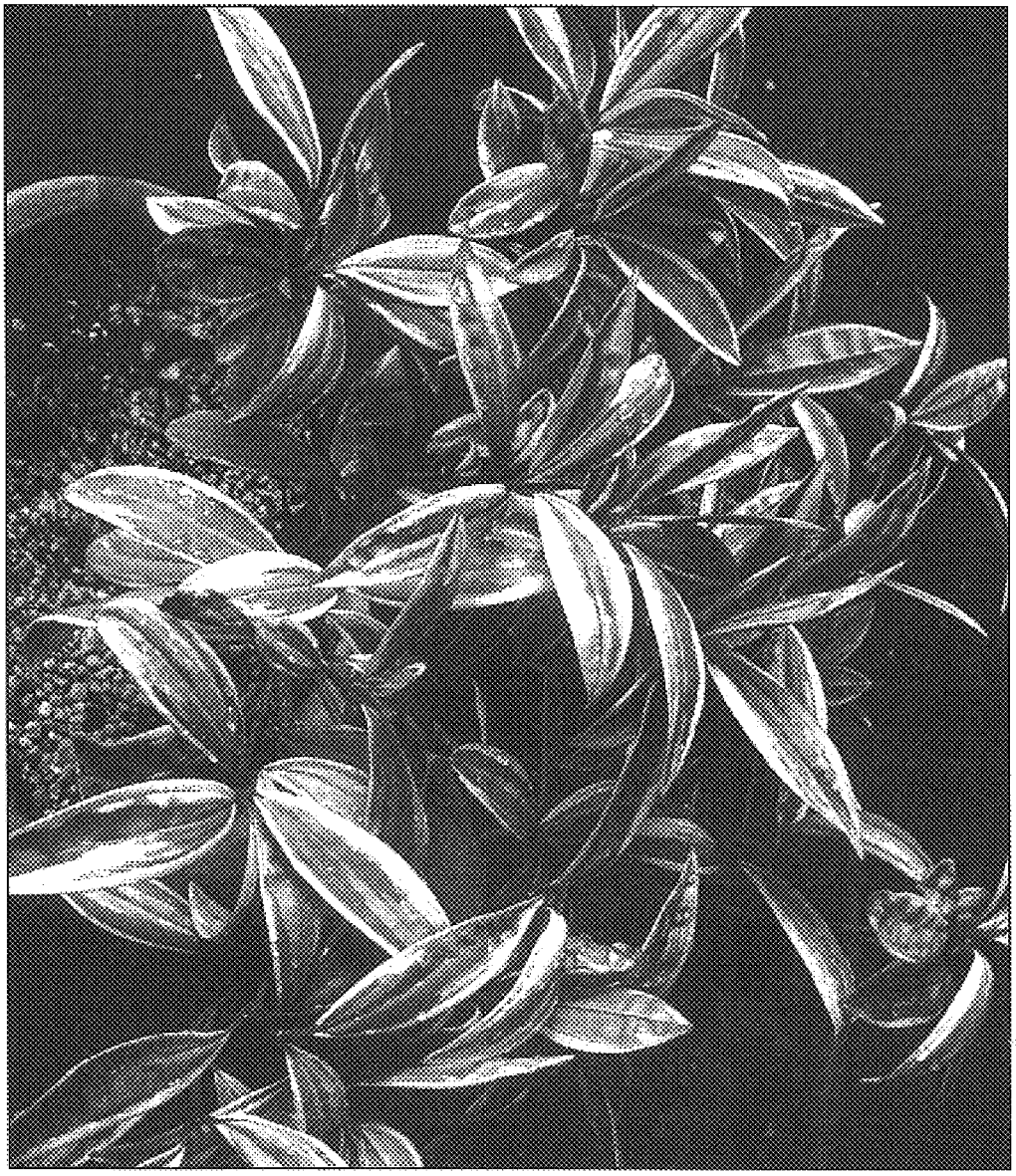
FIG. 1 illustrates the distinctive foliage variegation of the new variety.

*Pachycentria formosana* 'Gifu Variegated' has not been observed under all possible environmental, cultural and light conditions. The following observations and descriptions are of plants grown in Vacaville, Calif. and Lewisberry, Pa. Phenotypic expression may vary with light intensity, cultural, and environmental conditions. In this description, color references are to The Royal Horticultural Society Colour Chart (2001) and terminology used in the color descriptions herein refers to plate numbers in this color chart. As with many plants in the Melastomataceae family phenotypic characteristics can be dramatically different in terms of growth morphology.

Parentage: Branch sport of unnamed plant of *Pachycentria formosana.*

*Propagation.*—Stem cuttings.

*Time to initiate roots.*—About 14 days at 22 C.

*Time to develop roots.*—About 42 days at 22 C.

*Root appearance.*—Fibrous, freely branching.

Plant:

*Age of observed plant.*—2-year-old specimen in a 1-gallon nursery container.

*Size.*—Mature plant: Compact to 60 cm tall and wide. Observed: 18 cm.

*Branching observed quantity.*—6.

*Branch size observed.*—15 cm.

*Branch diameter.*—2 mm.

*Branch texture.*—Scabrous; irregular tiny scale-like hairs.

*Branch coloration young stems.*—Near Red Group 53B.

*Mature stems.*—Near Greyed-Orange Group 177A to 177B.

*Habit.*—Upright, somewhat outwardly spreading and open habit; sub-shrub.

Leaf:

*Shape.*—Nearly elliptic to elliptic.

*Apex.*—Acute to acuminate.

*Base.*—Attenuate.

*Margin.*—Entire, revolute.

*Texture.*—Smooth.

*Substance.*—Firm.

*Pattern of variegation.*—Broadly marginal with occasional irregular stripes invading the center of leaf, occasionally following the midrib.

*Leaf color.*—Varies with intensity of sunlight and cultural conditions; the following color readings were taken on Dec. 14, 2001, in Vacaville, Calif. of a specimen grown in a 1-gallon nursery container, in an unheated greenhouse at an average temperature of 70° F.

*Young Leaves.*—Green Sections Upper Side: Near Green Group 146B. Underside: Near Yellow-Green Group 148B. Variegated Sections Upper Side: Near Red Group 51C. Under Side: Near Red Group 51C.

*Mature foliage.*—Green Sections Upper Side: Plant displays 2 segments of variegation; near Yellow-Green Group 148C and near Green Group 138B. Underside: Near Yellow-Green Group 148D; bottom of leaf margin on mature foliage exhibits coloration near Red Group 51C.

*Variegated sections.*—Upper Side: Near White Group N155B. Underside: Near White Group N155D. Lateral Branches Quantity: Freely branching; pinching enhances lateral branch development. Diameter: About 5.5 mm. Texture: Scabrous; irregular tiny scale-like hairs. Venation Pattern: Parallel; 3 veins; impressed on upper side, raised on underside.

*Petioles.*—Size: 1 to 2 cm long. Coloration Upper Surface: Near Red-Purple Group 61B. Lower Surface: Near Red Group 53B.

*Internodes.*—2.5 cm.

*Leaf size.*—7.5 to 9.5 cm long; 2 to 3 cm wide.

Hardiness: USDA Zone 10 (30° to 40° F.).

Vigor: Moderate.

Pests/diseases: No susceptibility or resistance to disease beyond that of the species has been noted.

Infloresence:

*Bloom period.*—May through September.

*Flower arrangement.*—Terminal cymes.

*Flower form.*—Radial, 4-petaled.

*Flower size.*—3.5 to 4 cm in diameter.

*Lastingness of individual blooms.*—5 to 7 days.

*Fragrance.*—None noted.

*Petals.*—Coloration Upper Surface: Near Purple-Violet Group N82B. Length/Width: 1.75 to 2 cm long; 1 to 1.5 cm wide.

*Base.*—Truncate.

*Apex.*—Obtuse.

*Aspect.*—Incurved tips.

*Margins.*—Entire.

Buds:

*Coloration.*—Near Purple-Violet

*Apex.*—Obtuse.

*Aspect.*—Incurved tips.

*Margins.*—Entire.

Buds:

*Coloration.*—Near Purple-Violet Group N32D.

Reproductive organs:

*Stamens.*—Number: 8. Length: 5 mm to 7 mm.

*Anther.*—Length: 1 mm.

*Pistil.*—Number: 1, strongly and abruptly upcurved from the base. Length/width: 8 mm long; 1 mm wide.

I claim:

1. A new variety of *Pachycentria formosana* plant of the variety substantially as shown and described.

* * * * *

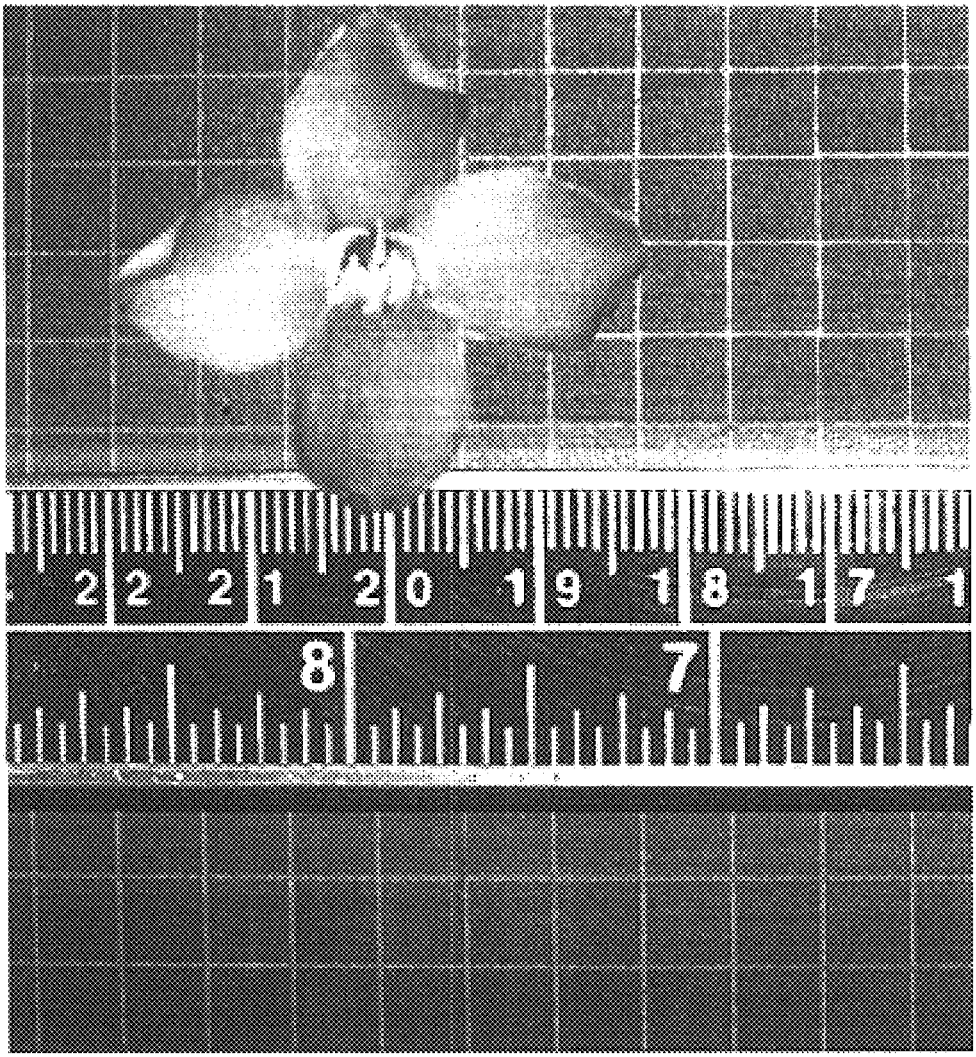
2 2 2 1 2 0 1 9 1 8 1 7 1
8
7